(12) United States Patent
Goetzinger et al.

(10) Patent No.: US 11,998,408 B2
(45) Date of Patent: Jun. 4, 2024

(54) PROCESS OF MANUFACTURING A DENTAL MILLING BLOCK WITH A HOMOGENEOUS COLOR AND/OR TRANSLUCENCY GRADIENT

(71) Applicant: Solventum Intellectual Properties Company, Maplewood, MN (US)

(72) Inventors: Martin Goetzinger, OT Pflugdorf (DE); Hans R. Schnagl, Jengen (DE)

(73) Assignee: Solventum Intellectual Properties Company, Maplewood, MN (US)

(*) Notice: Subject to any disclaimer, the term of this patent is extended or adjusted under 35 U.S.C. 154(b) by 0 days.

(21) Appl. No.: 18/015,338

(22) PCT Filed: Jul. 19, 2021

(86) PCT No.: PCT/IB2021/056521
§ 371 (c)(1),
(2) Date: Jan. 10, 2023

(87) PCT Pub. No.: WO2022/023871
PCT Pub. Date: Feb. 3, 2022

(65) Prior Publication Data
US 2023/0270529 A1    Aug. 31, 2023

(30) Foreign Application Priority Data

Jul. 29, 2020 (EP) .................................. 20188292

(51) Int. Cl.
*A61C 13/00* (2006.01)
*A61K 6/802* (2020.01)
(Continued)

(52) U.S. Cl.
CPC .......... *A61C 13/0022* (2013.01); *A61K 6/802* (2020.01); *B01F 23/60* (2022.01);
(Continued)

(58) Field of Classification Search
CPC ............................. B01F 23/60; A61C 13/0022
See application file for complete search history.

(56) References Cited

U.S. PATENT DOCUMENTS

| 6,354,836 | B1 | 3/2002 | Panzera et al. |
| 7,985,119 | B2 | 7/2011 | Basler et al. |
| (Continued) | | | |

FOREIGN PATENT DOCUMENTS

| CN | 103273713 B | * 12/2015 |
| CN | 104909745 B | 3/2017 |
| (Continued) | | |

OTHER PUBLICATIONS

1507 Extended EP Search Report for EP20188292.5, dated Nov. 17, 2020, 4pgs.
(Continued)

*Primary Examiner* — Cachet I Proctor
(74) *Attorney, Agent, or Firm* — Kevin Weber

(57) ABSTRACT

The invention relates to a process of manufacturing a dental milling block with a homogeneous color and/or translucency gradient. This process comprises the steps of providing a mold with a cavity having a z-direction and an x/y-direction, filling the cavity partially with a first powder up to a height H1, the first powder having a volume VP1 with a top and bottom surface, introducing a second powder on top of the first powder up to a height H2, the second powder having a volume VP2 with a top and bottom surface and, the top surface of the first powder being in contact with the bottom surface of the second powder and forming an intermediate region, providing a mixer unit with at least one rotatable mixing element, introducing the rotating mixing element in z-direction into the intermediate region, mixing the powder located in the intermediate region by rotating the mixing element, removing the rotating mixing element from the powder, compacting the powder, optionally applying heat to
(Continued)

the compacted powder, the first powder differing from the second powder by its physical properties and/or chemical composition and/or color. The invention also relates to a process of producing a dental restoration using dental milling block obtainable according to this process.

15 Claims, 10 Drawing Sheets

(51) Int. Cl.
    *B01F 23/60* (2022.01)
    *B01F 27/231* (2022.01)
    *B01F 27/806* (2022.01)
    *B28B 3/00* (2006.01)
    *B28B 11/24* (2006.01)

(52) U.S. Cl.
    CPC ........ *B01F 27/2312* (2022.01); *B01F 27/806* (2022.01); *B28B 3/00* (2013.01); *B28B 11/24* (2013.01)

(56) References Cited

U.S. PATENT DOCUMENTS

| | | |
|---|---|---|
| 8,025,992 B2 | 9/2011 | Engels et al. |
| 8,141,217 B2 | 3/2012 | Gubler et al. |
| 10,028,809 B2 | 7/2018 | Jahns et al. |
| 10,219,880 B2 | 3/2019 | Rolf et al. |
| 10,245,127 B2 | 4/2019 | Kim et al. |
| 10,441,391 B2 | 10/2019 | Volkl et al. |
| 2013/0344221 A1 | 12/2013 | Farrell et al. |
| 2014/0377718 A1 | 12/2014 | Korten et al. |
| 2015/0137404 A1* | 5/2015 | Tuchinskiy ............... B22F 7/06 264/642 |
| 2017/0273764 A1* | 9/2017 | Volkl ....................... A61K 6/78 |
| 2018/0327319 A1* | 11/2018 | Li .......................... A61K 6/818 |
| 2019/0231494 A1 | 8/2019 | Dittmann et al. |
| 2019/0233340 A1 | 8/2019 | Kim et al. |

FOREIGN PATENT DOCUMENTS

| | | | |
|---|---|---|---|
| CN | 108585845 A | 9/2018 | |
| DE | 20316004 U1 | 3/2004 | |
| EP | 1859758 A1 | 11/2007 | |
| EP | 2472227 A2 | 7/2012 | |
| EP | 3108849 A1 * | 12/2016 | ......... A61C 13/0022 |
| EP | 3108849 A1 | 12/2016 | |
| WO | 2001013862 A1 | 3/2001 | |
| WO | 2002045614 A1 | 6/2002 | |
| WO | WO-2007069623 A1 * | 6/2007 | ............... A61F 2/28 |
| WO | 2017114772 A1 | 7/2017 | |

OTHER PUBLICATIONS

International Search Report for PCT International Application No. PCT/IB2021/056521, dated Oct. 7, 2021, 4 pages.

* cited by examiner

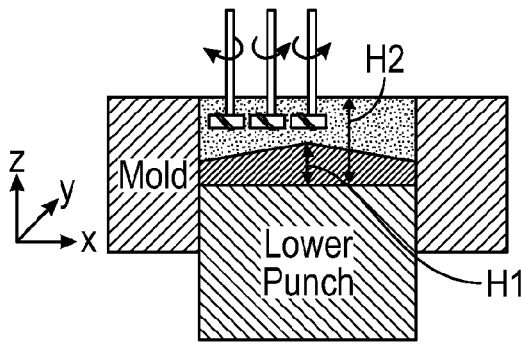
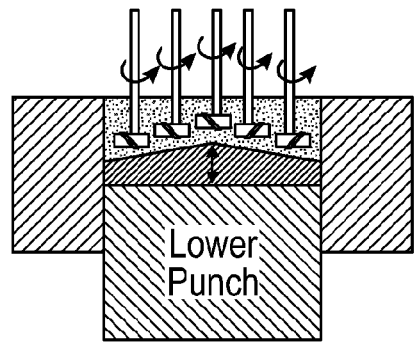
FIG. 3A
FIG. 3B
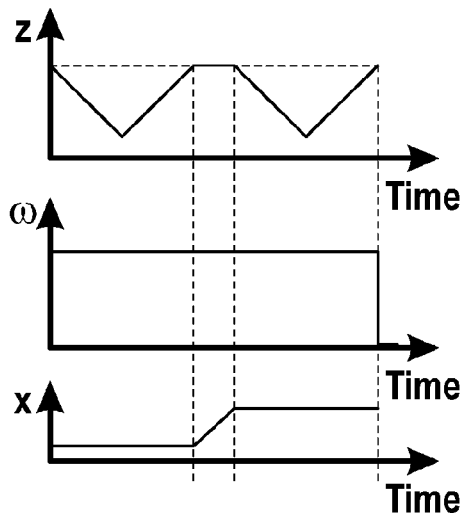
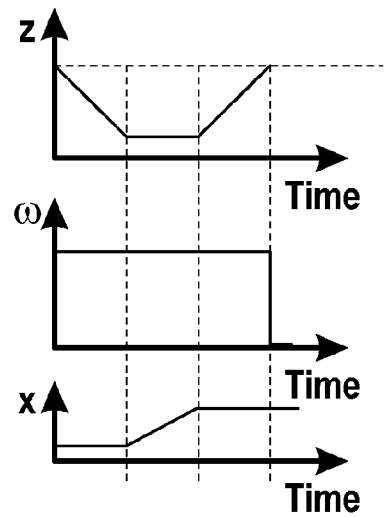
FIG. 4A
FIG. 4B
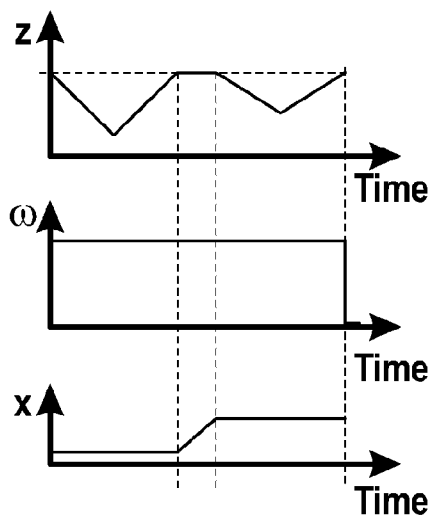
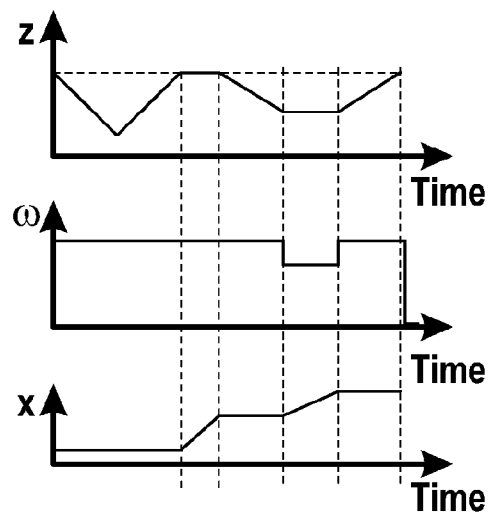
FIG. 4C
FIG. 4D

PROCESS OF MANUFACTURING A DENTAL MILLING BLOCK WITH A HOMOGENEOUS COLOR AND/OR TRANSLUCENCY GRADIENT

CROSS REFERENCE TO RELATED APPLICATIONS

This application is a national stage filing under 35 U.S.C. 371 of PCT/IB2021/056521, filed Jul. 19, 2021, which claims the benefit of European Application No. 20188292.5, filed Jul. 29, 2020, the disclosures of which are incorporated by reference in their entireties herein.

FIELD OF THE INVENTION

The invention relates to a process of manufacturing a dental milling block with a homogeneous color and/or translucency gradient. The dental milling block can be used for producing highly aesthetic dental restorations.

BACKGROUND

For producing highly aesthetic dental restorations the individually colored dental situation in the mouth of a patient has to be taken into account.

In trying to mimic the natural appearance of a dental tooth, dental milling blocks with a color gradient are meanwhile commercially available from which a dental restoration is to be milled and sintered.

Different concepts for producing these kinds of dental milling blocks are described in the art.

One concept is focusing on using coloring liquids which are applied to a porous dental milling block. During the application process a kind of color gradient is developed caused by the coloring ions present in the coloring liquid and being absorbed by the porous dental milling block.

E.g. CN 104 909 745 BB (Chengdu Besmile Biotech.) describes a preparation method to obtain uniform gradient-color zirconium oxide porcelain blocks. The preparation method comprises the steps: (1) weighing the raw materials of $CeO_2$, $Fe_2O_3$, $ZrO_2$, $Y_2O_3$, $Pr_6O_{11}$ and $Er_2O_3$; (2) adding a polymer binder, and granulating; (3) shaping the granulated material; (4) carrying out isostatic cool pressing; (5) pre-sintering the porcelain block blanks; (6) flatly placing the pre-sintered porcelain block blanks in a dyeing container and dyeing, wherein certain conditions are applied; and (7) sintering the dyed porcelain blocks to obtain the uniform gradient-color zirconium oxide porcelain blocks for dentistry.

CN 108 585 845 A (Bloomden Bioceramics) describes a method for preparing a zirconium oxide ceramic blank with gradual change of color and permeability. The method comprises the steps: (1) preparing a soluble yttrium solution, soaking one side of a pre-sintered zirconium oxide ceramic into a solution liquid level, exerting negative pressure to the other side of the zirconium oxide ceramic, and controlling a reduction velocity of the solution liquid level according to a preset pressure-time curve till the liquid level is reduced to a zero liquid level; (2) preparing a user-made 16-color dyeing solution which meets 16 vita colors or a user-made 26-color dyeing solution which meets 26 vita colors, turning over the dried zirconium oxide ceramic for 180°, soaking one side of the zirconium oxide ceramic into a dyeing solution liquid level, exerting negative pressure to the other side of the zirconium oxide ceramic, and controlling a reduction velocity of the liquid level according to a preset pressure-time curve until the liquid level is reduced to a zero liquid level.

US 2019/0233340 A1 (Kim et al.) describes a method of coloring a ceramic body for use in dental applications. The method comprises the steps of obtaining a porous ceramic body comprising first and second end surfaces and a side surface, contacting various portions of the ceramic body with a casing material, infiltrating a diluting liquid to occupy a first porous region, adjusting the casing, infiltrating a liquid coloring composition to occupy a second porous region, wherein the casing material prevents the liquid coloring composition and diluting liquid from passing through the first end surface and side surface.

Another concept is focusing on layering differently colored powder compositions one over the other and compacting the powder composition afterwards.

EP 3 108 849 A1 (3M) relates to a porous multi-layered colored zirconia dental mill blank comprising two different layer with compositions B and E arranged in alternating order, wherein the thickness of the individual layers with composition B is decreasing from bottom to top and the thickness of the individual layers with composition E is decreasing from top to bottom.

U.S. Pat. No. 10,245,127 B2 (Kim et al.) describes a method of manufacturing a multilayer zirconia block for artificial teeth, including a first material mixing step, a second material mixing step, a third material mixing step, a compression molding step, and a calcination step. This method is said to provide a multilayer zirconia block that contains yttrium oxide, the amount of which is adjusted in the manufacturing process, thus showing a color similar to that of natural teeth after impregnation with a coloring solution.

Yet a further concept is suggesting the use of a mixer for mixing powder compositions.

U.S. Pat. No. 10,441,391 B2 (Volkl et al.) describes a method to manufacture a colored zirconia blank whereby raw materials in powder form are mixed, the resulting mixture pressed and subsequently subjected to a thermal treatment. One of the powder mixtures to be mixed contains a coloring substance. After introduction of a first powder layer, another less colored material is filled in the mold to form an intermediate layer which mixed with the first layer. Subsequently a further layer is filed in the mold which has a higher yttrium oxide content than the first layer.

Further dental milling blocks with different layers or regions are described e.g. in U.S. Pat. No. 10,219,880 (Rolf et al.). The dental mill blank includes a first layer of a first hard restorative material having a first translucency and a first shade, a second layer of a second hard restorative material having a second translucency and a second shade, where at least one of the following is true (1) the first translucency is different from the second translucency, (2) the first shade is different from the second shade. The first layer and the second layer form a first interface having a first curve across a first plane of symmetry of the dental mill blank, where the first curve has a different from zero curvature; and a first straight line along the entire length of a second plane of the dental mill blank, the second plane being orthogonal to the first plane of symmetry.

U.S. Pat. No. 10,028,809 A1 (Jahns et al.) relates to a porous dental milling block comprising at least two geometrically defined material sections A and B comprising tetragonal crystal phases and cubic zirconia crystal phases in different amounts.

SUMMARY OF INVENTION

None of the described process is completely satisfying. There is still a need for alternatives, which may help to either simplify or improve the existing processes.

In particular, the various layers of different powder components are sometimes still visible.

Thus, there is a need for a dental milling block having a more homogenous color gradient.

If possible, the process of producing such a dental milling block should not be too complicated.

In one embodiment the invention features a process of manufacturing a dental milling block, the process comprising the steps of
 i. providing a mold with a cavity having a z-direction and an x/y-direction,
 ii. filling the cavity partially with a first powder up to a height $H_1$, the first powder having a volume $V_{P1}$ with a top and bottom surface,
 iii. introducing a second powder on top of the first powder up to a height $H_2$, the second powder having a volume $V_{P2}$ with a top and bottom surface and,
  the top surface of the first powder being in contact with the bottom surface of the second powder and forming an intermediate or interface region,
 iv. providing a mixer unit with at least one rotatable mixing element,
 v. introducing the rotating mixing element in z-direction into the intermediate region typically at time $t_{start}$,
 vi. mixing the powder located in the intermediate region by rotating the mixing element typically for a time $t_{mix(x,y,z)}$ thereby forming a continuous transition region due to the movement of the rotating mixing element from already mixed region into unmixed region and continuing the mixing for a time $t_{mix(x',y',z')}$,
 vii. removing the rotating mixing element from the powder typically at time tend,
 viii. compacting the powder preferably by applying pressure of 10 to 300 MPa for 0.5 s to 5 min,
 ix. optionally applying heat to the compacted powder preferably by applying a heating ramp followed by a dwell temperature of 800 to 1,100° C. at ambient conditions for 5 to 300 min,
the first powder differing from the second powder by its physical properties and/or chemical composition and/or color.

The invention is also directed to a process of producing a dental restoration obtained by machining it from the dental milling block described in the present text and to the dental restoration obtained by such a process.

A further aspect of the invention is directed to a kit of parts comprising a mold as described in the present text, a mixer unit as described in the present text, a first and a second powder in the present text.

Unless defined differently, for this description the following terms shall have the given meaning:

The term "dental restoration" means an article which is to be used in the dental field to restore a defect tooth structure. The dental restoration typically has a 3-dimensional inner and outer surface. The surface typically includes convex and concave structures. Compared to other articles such as pottery or paving stones, a dental restoration is small and filigree. The thickness of the dental restoration can vary from very thin, e.g. at the edges and rims (below 0.1 mm) to considerably thick, e.g. in the biting area (up to 8 or 16 mm). Sections bridging the crown portions in dental bridges might have a thickness up to 20 mm. The outer surface typically has an overall convex shape, whereas the inner surface typically has an overall concave shape.

The dental restoration described in the present text comprises or essentially consists after sintering of a polycrystalline ceramic material comprising yttrium stabilized zirconia.

Examples of dental restorations include crowns (including monolithic crowns), bridges, inlays, onlays, veneers, facings, crown and bridged framework, abutments, orthodontic appliances (e.g. brackets, buccal tubes, cleats and buttons), and parts thereof.

The surface of a tooth is not regarded a dental article or dental restoration.

A dental restoration should not contain components which are detrimental to the patient's health and thus free of hazardous and toxic components being able to migrate out of the dental restoration.

By "dental milling blank or dental milling block" is meant a solid block (3-dim article) of material from which a dental restoration can and typically is to be machined in a subtractive process, e.g. aside from milling also by grinding, drilling etc. A dental mill blank has a geometrically defined shape and comprises typically two opposing flat surfaces. A so-called "free form surface" is not regarded as "geometrically defined". In this respect, the shape of a dental restoration (e.g. crown or bridge) itself is not regarded a dental mill blank.

"Zirconia article" shall mean a 3-dimensional article wherein at least one of the x,y,z dimensions is at least 5 mm, the article being composed of at least 80 or at least 90 or at least 95 wt. % zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monoclinic, cubic zirconia and mixtures thereof.

"Homogeneous color and/or translucency gradient" means a set of colors or translucency or a combination of color and translucency arranged in a linear, not stepped or staggered order. The gradient can be axial, radial or conical in 1 dimension, 2 dimensions or 3 dimensions.

If desired, the presence of a homogeneous color gradient can be examined visually or more precisely by using an image analysis software (e.g. ImageJ) as described in the example section.

A "mold" is a block with a hollow cavity intended to be filled with a material which is typically compacted or solidified afterwards.

A "powder" means a dry, bulk composed of a large number of particles that may flow freely when shaken or tilted.

A "particle" means a substance being a solid having a shape which can be geometrically determined. The shape can be regular or irregular. Particles can typically be analysed with respect to e.g. size and size distribution.

The particle size (d50) of a powder can be obtained from the cumulative curve of the grain size distribution. Respective measurements can be done using commercially available granulometers. "D" represents the diameter of powder particles and "50" refers to the volume percentage of the particles. Sometimes, the 50% is also expressed as "0.5". For example, "(d50)=1 μm" means that 50% of the particles have a size of 1 μm or less.

"Density" means the ratio of mass to volume of an object. The unit of density is typically g/cm³. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the material can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics.

The terms "sintering" or "firing" are used interchangeably. A porous ceramic article shrinks during a sintering step, that is, if an adequate temperature is applied. The sintering temperature to be applied depends on the ceramic material chosen. For zirconia based ceramics a typical sintering temperature range is 1,100° C. to 1,600° C. If the sintering is done with high heating-rates, higher temperatures may be required. Sintering typically includes the densification of a porous material to a less porous material (or a material having less cells) having a higher density, in some cases sintering may also include changes of the material phase composition (for example, a partial conversion of an amorphous phase toward a crystalline phase).

A dental zirconia article is classified as "pre-sintered", if the dental zirconia article has been treated with heat (temperature range of 900 to 1,100° C.) typically for 1 to 3 h to such an extent that the biaxial flexural strength of the dental ceramic measured according to the "punch on three ball test" ISO 6872:2015 is within a range of 8 to 80 MPa or 15 to 55 MPa.

A pre-sintered dental ceramic usually has a porous structure and its density (usually about 3.0 g/cm³ for an yttrium stabilized zirconia ceramic) is less compared to a completely sintered dental ceramic framework (usually about 6.1 g/cm³ for an yttrium stabilized zirconia ceramic).

"Coloring ions" shall mean ions which have an absorption in the spectral range visible to the human eye (e.g. 380 to 780 nm), which may result in a colored solution (visible to the human eye), if the coloring ions are dissolved in water (e.g. about 0.6 mol/l) and especially cause a coloring effect in the zirconia article which has been treated with a coloring solution and sintered afterwards. Coloring ions may also be present (typically as component of a salt or oxide) in the powder before the powder, which is used for producing the zirconia article, is compacted.

A "fluorescing agent or component" shall mean an agent capable to impart fluorescence, measurable as light emission in the region of visible light (380 to 780 nm).

By "machining" is meant milling, grinding, cutting, carving, or shaping a material by machine. Milling is usually faster and more cost effective than grinding. A "machinable article" is an article having a 3-dimensional shape and having sufficient strength to be machined.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory, ambient conditions are typically adjusted to 20 to 25° C., 1000 to 1025 mbar and 40 to 60% relative humidity.

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

"And/or" means one or both. E.g., the expression component A and/or component B refers to a component A alone, component B alone, or to both component A and component B.

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The terms "comprise" or "contain" and variations thereof do not have a limiting meaning where these terms appear in the description and claims. The term "comprise" shall include also the terms "consist essentially of" and "consist of". "Consisting essentially of" means that specific further components can be present, namely those which do not materially affect the essential characteristic of the article or composition. "Consisting of" means that no further components should be present.

BRIEF DESCRIPTION OF FIGURES

FIG. 3 (a-b) shows another arrangement of mixers which can be used for the process described in the present text.

FIG. 4 (a-d) exemplifies possible mixing profiles (relationship between rotation speed of the mixing element and its x-/z-location within the cavity of the mold.

FIG. 7 (c-d) shows an image of an inventive dental milling block and a related plot profile.

DETAILED DESCRIPTION

Figure 1A:
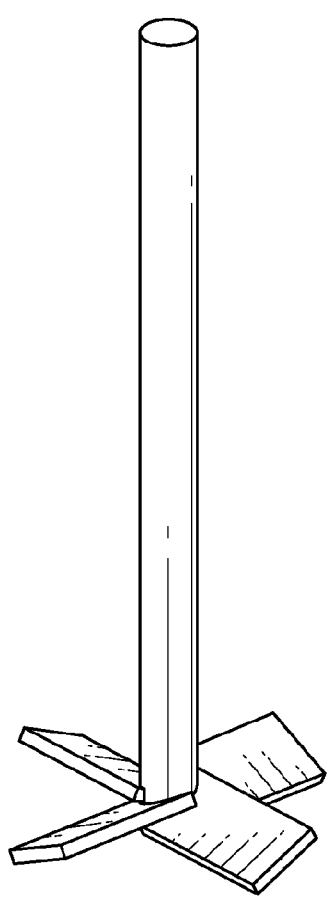
FIG. 1 (a-f) shows different mixers which can be used for the process described in the present text.

It has been found that the composition described in the present text has a couple of advantageous properties.

Using a mixing element for mixing powder compositions is generally know. However, it was surprising found that it is also possible to mix powders in a controlled manner which are located only in a certain region or position of a bigger volume thereby producing a gradient within the powder composition.

In particular this can be achieved, if the mixing element used for mixing the powder compositions is rotating not only during the mixing step but already at the step when the mixing element is introduced in the powder composition to be mixed and continues rotating when it is removed from the mixed powder composition.

While rotating, the mixing element already conveys powder from the upper region of the powder composition to the intermediate or interface region where the two powders to be mixed contact each other. Similarly, while rotating the mixing element coveys already mixed powder to the upper region of the powder composition which contributes to a smooth gradient.

If the mixing element is not rotating when it is introduced in the powder composition, the powder composition may already be slightly compacted, which can be contra productive during the later mixing process.

If the mixing element is not rotating when it is removed from the mixed powder composition, it was observed that the mixed powder composition is often dissipated or moved to other regions of the powder composition which are not intended to be mixed.

Thus, by using a mixing element which is not only rotating when introduced into the region of a powder composition to be mixed, but also when the mixing element is removed from the mixed powder composition, a homogeneous powder gradient can be obtained in a defined region of the powder composition to be mixed.

It was surprising that this effect can also be achieved for small volumes of powder compositions.

The invention described in the present text relates to process of manufacturing a dental milling block. The process comprises a couple of steps.

In a first step, a first volume $V_{P1}$ of a first powder (e.g. powder A) is filled into the cavity of a mold.

The mold has a cavity with a vertical z-direction and a horizontal x/y direction perpendicular to the z-direction. In z-direction there is an opening into the cavity of the mold for receiving the powders to be mixed. The shape and size of the cavity of the mold typically essentially corresponds to the shape of the dental milling block to be produced. In many cases the cavity of the mold has a cylindric or cubic or cuboid shape. If desired, other shapes can be used too, including horseshoe shaped, elliptical, spherical and others. For producing dental milling blocks, the volume of the cavity of the mold is typically in a range of 2 to 2,000 ml or 5 to 500 ml or 10 to 300 ml.

The filling of the powder composition into the cavity of the mold can be done with various means including a vibration feeder, screw feeder or by using a fill shoe, wherein using a fill shoe is sometimes preferred as it allows an easy filling of the mold layer by layer.

In a further step a second volume $V_{P2}$ of a second powder (e.g. powder B) is filed into the cavity on top of the first powder.

The first powder is filled in the cavity of the mold up to a height $H_1$. The height $H_1$ represents the upper level of the first powder. The height $H_1$ is typically in a range of 1 to 99 or 1 to 90 or 2 to 80 mm or 2 to 70 mm.

The second powder is filled in the cavity of the mold up to a height $H_2$. The height $H_2$ represents the upper level of the powder composition filled into the cavity of the mold. The height $H_2$ is typically in a range of 25 to 100 or 30 to 90 mm or 40 to 80 mm.

Depending on the means or element used for filling the powders into the cavity of the mold, the height in x and y direction especially for the first powder might not be uniform. The height can be a function of x and y: $H_{1(x,y), 2(x,y)}$. The top surface of the powder composition filled into the cavity of the mold is typically flat.

According to one embodiment, first powder and the second power form layers which are typically parallel to each other. The filling of the powders layer by layer can be preferred, if the height z of the dental milling block to be produced is smaller than its dimensions in x/y direction, e.g. if the dental milling block has the shape of a disc.

According to another embodiment, the first powder forms a cone with a height $H_1$ within the mold and the second powder is applied on top of the first powder filling the remaining space between the cone surface and the mold boundaries up to the height $H_1$ and an additional layer of the second powder is applied on top up to the height $H_2$.

A cone-shaped filling of the first powder into the mold can be desired as it might help to better mimic or imitate the appearance of a natural tooth which has an inner dentin portion and an outer enamel portion which is more translucent than the dentin portion. If the first powder forms a cone intended to imitate the dentin portion of the dental restoration to be produced later, the color and/or translucency of the first powder after sintering is typically darker and/or less translucent compared to the second powder.

If desired even more complex surface geometries can be produced by e.g. using vibration or screw feeders.

According to one embodiment, only two different powders A and B are used, but it can also be desirable to fill additional powders into the mold, e.g. a powder C with a third volume and/or a powder D with a fourth volume.

The individual volumes of the powders $V_{P1}$ and $V_{P2}$ can be same or different. If they are different, the volumes typically differ from each other by not more than 5 to 60% or 10 to 50% or 15 to 40%.

The volumes of the powders to be used typically depends on the size and volume of the dental milling block to be produced.

As the powders are filled into the cavity of the mold in powder form, volume refers to the bulk volume of the powders. The bulk volume for the individual powders is typically in a range of 0.9 to 2 $g/cm^3$ or 1 to 1.8 $g/cm^3$.

The first powder and the second powder differ from each other with respect to its physical properties and/or chemical composition and/or color, wherein the difference in chemical composition and/or color is sometimes preferred.

The chemical components of the powders are further described in the text below. The chemical composition can also affect the translucency of the sintered product.

According to a preferred embodiment, the powders differ from each other with respect to color. A difference in color can be achieved, e.g. by using a different amount of coloring components, or by using different coloring components, or a mixture of both.

According to another embodiment, the powders comprise ceramic components and stabilizing components and differ from each other with respect to the content of the stabilizing components.

The process for manufacturing a dental milling block also comprises the step of providing a mixer unit. The mixer unit typically contains a motor for driving a mixer shaft which contains mixing elements or to which mixing elements are attached. Depending on the shape of the mixer shaft, the mixing elements can form a part of the mixer shaft.

The mixing elements should have a form or shape enabling the controlled local transport or movement of the powders to be mixed at least in z-direction of the mold. The mixing elements can have different shapes, e.g. a helical or spiral shape, the shape of a single blade, multiple blades, screw, auger or a combination thereof. If the mixing element has the shape of a blade, the blade is typically angled.

The mixer shaft contains at least one mixing element. If the mixer shaft contains more than one mixing element (e.g. 2 to 8 or 3 to 6), the mixing elements are typically arranged symmetrical to each other. However, it is also possible that the mixing elements are located at the mixing shaft in different heights or not symmetrical.

Compared to mixers described in the prior art, the mixing shaft described in the present text is rather short. A typical length of the mixer shaft is in a range of 0.5 to 15 cm or 1 to 10 cm or 2 to 8 cm or 3 to 6 cm.

Figure 1B:
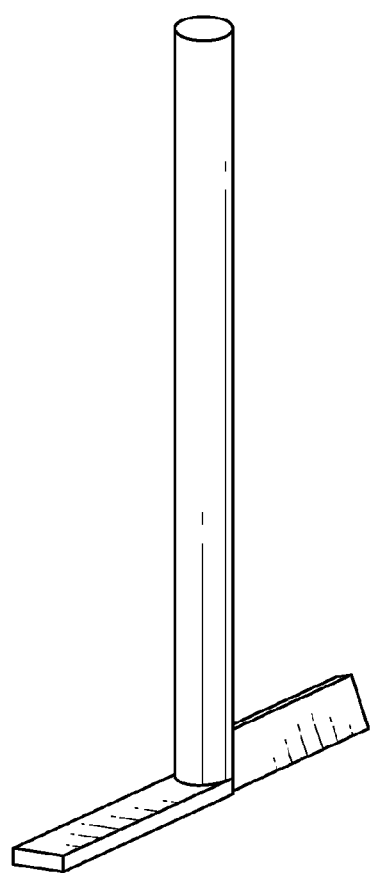
Figure 1C:
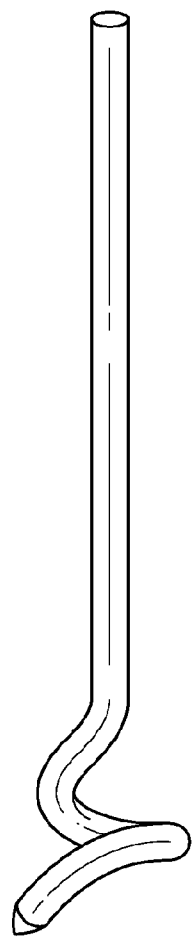
Figure 1D:
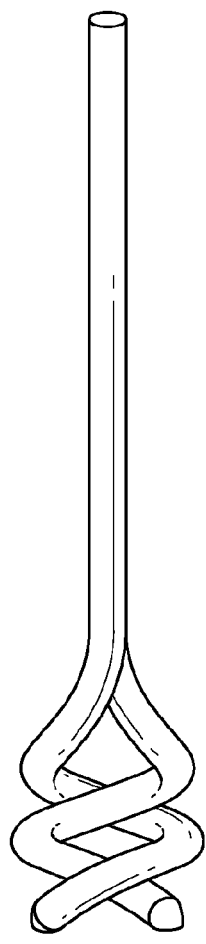
Figure 1E:
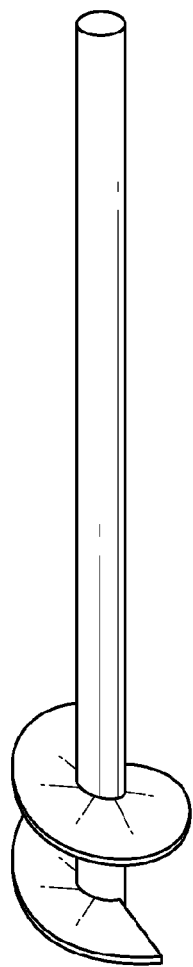
Figure 1F:
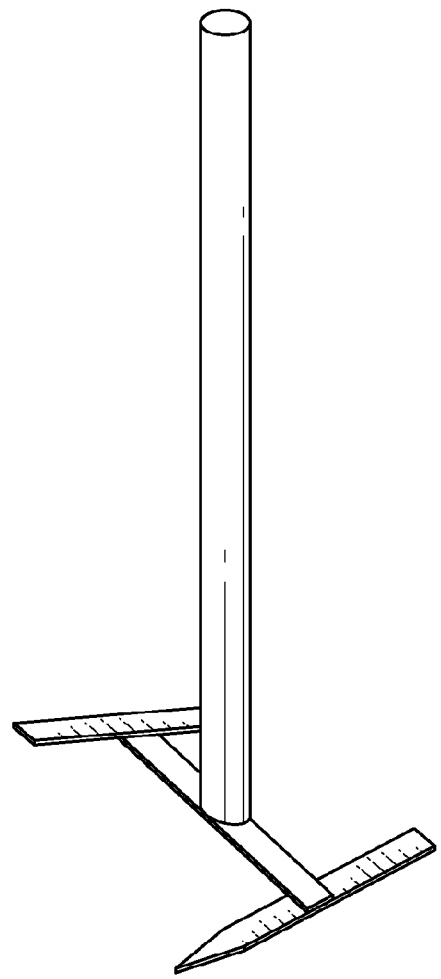

Possible shapes of mixing elements are shown in FIG. 1a to FIG. 1f. FIG. 1a shows a mixer with a rotor shaped mixing element with four blades. FIG. 1b shows a mixer with a rotor shaped mixing element with two blades. FIG. 1c shows a mixer with a hollow helical mixing element. FIG. 1d shows a mixer with a crossed helical element. FIG. 1e shows a mixer with a screw conveyor shaped or auger shaped mixing element. FIG. 1f shows a mixer with two angled blades spaced apart from the mixing shaft.

The mixer unit can contain more than one mixer shaft. The number of mixer shafts and correspondingly the number of mixing elements is not particularly limited but typically related to the size and dimension of the cavity of the mold containing the powders to be mixed. For a larger size or volume of powders to be mixed it can be beneficial if the mixer unit contains 2 to 30 or 3 to 20 mixer shafts.

The mixer shafts can be arranged in different patterns. An arrangement in a circular, triangle, square, rectangular or polygonal (e.g. 5, 6, 7 or 8) pattern can be beneficial. It can be preferred, if a pattern is used which covers essentially the complete area of the powders to be mixed. In this respect, the use of differently sized mixing elements can be useful. Such an arrangement can be advantageous as a movement of the mixing elements in horizontal direction might not be needed any longer and the mixing process can be done in a shorter period of time.

Figure 2A:
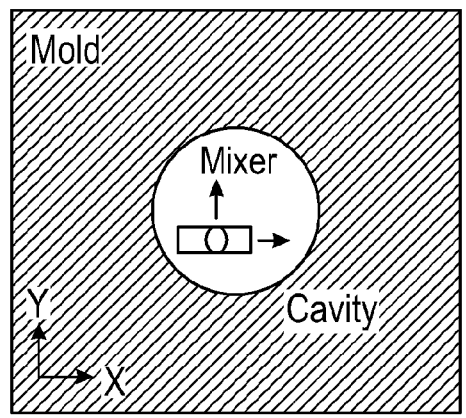
FIG. 2 (a-d) shows different patterns of arrangement of mixers which can be used for the process described in the present text.
Figure 2B:
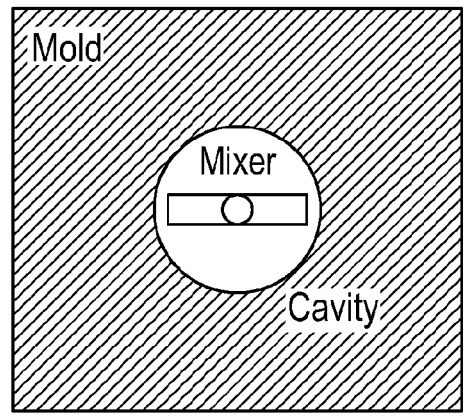
Figure 2C:
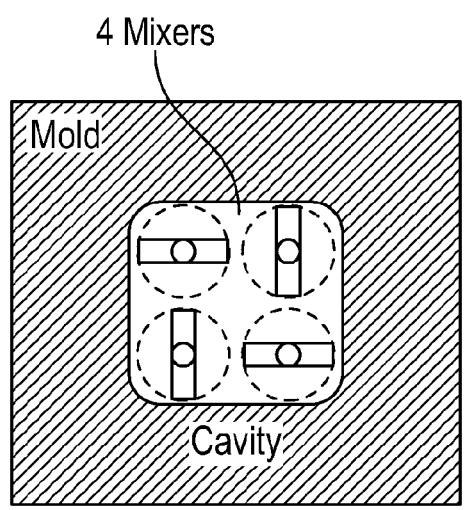
Figure 2D:
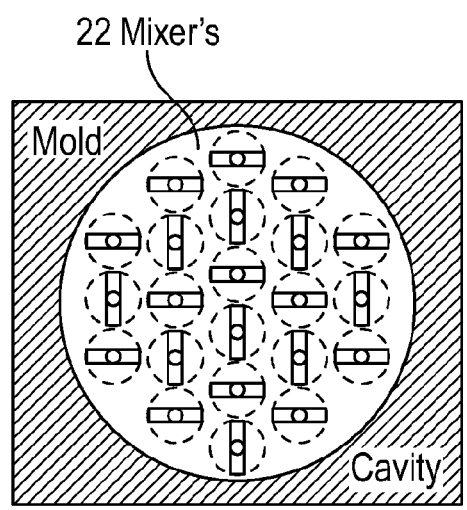

Possible patterns how the mixing shafts can be arranged are shown in FIGS. 2a to 2d. FIG. 2a shows a mold (dark grey area) with a circular cavity (light grey area) in x/y-direction. Located within the cavity is a mixer with a double-bladed mixing element which is moveable in x/y- and z-direction. In FIG. 2b the mixing element is larger and not moveable in x/y-direction. In FIG. 2c a rectangular cavity with rounded edges in the mold is shown. Located within the cavity are four mixers with double-bladed mixing elements. The mixing elements are moveable essentially in z-direction only. In FIG. 2d a circular cavity in the mold is shown. Located within the cavity are 22 mixers with double-bladed mixing elements. The mixing elements are moveable essentially in z-direction only.

The mixer(s) needs to be moveable at least in z-direction relative to the powder and mold. It can also be advantageous, if the mixer(s) is in addition moveable in x- or y-direction. It can also be advantageous, if the mixer(s) is individually moveable in z-, x- and y-direction.

If there are only a few (e.g. 2 to 4) or only one mixer shaft, it can also be beneficial, if the mixer shaft(s) is/are individually moveable horizontally (in x/y-direction of the cavity of the mold). If there are more mixer shafts, it can also be advantageous, if the mixer shafts are individually rotatable. The individual rotation of the mixer shafts can be clockwise or counter-clockwise. It is also possible, that the mixer shafts are rotating planetary gear like. Length and/or position of the mixing elements on the mixer shaft might be different.

FIG. 3a and FIG. 3b show an arrangement of mixers which can be used for the process described in the present text. FIG. 3a shows a mold in z-direction. Within the cavity of the mold the volume of which is adjusted by a lower punch is located a cone of a first powder (dark grey) up to a height of $H_1$. Above the first powder there is located a second powder up to a height $H_2$. Within the second powder three individual rotating mixers are located, wherein one mixer is rotating clockwise and the two other mixers are rotating counter-clockwise. FIG. 3b shows the same set-up, but with a different arrangement of the mixers. Five mixers are shown (rotating in the same direction) which are located at different levels of the second powder close to the intermediate or interface region.

The powders to be mixed in the intermediate region typically extend up to 90% or up to 80% or up to 70% or up to 60% or up to 50% of the overall height of the powder composition filled into the mold.

Once the mixing element has been introduced in the intermediate region of the powders to be mixed, the mixing element is typically not moved in z-direction over a distance of more than 50% of the height $H_1$ of the first powder.

The rotation speed to be used is typically also related to the shape and size of the mixing elements. For larger sized mixing elements typically a slower rotation speed is used. For mixing the powders described in the present text a rotation speed in the range of 10 to 10,000 or 20 to 1,000 or 30 to 800 rounds/min for the individual mixing shafts was found to be useful.

A too high rotation speed could negatively influence the desired color and/or composition gradient in the powder composition. Using a rather slow rotation speed can be beneficial to limit the mixing process to a particular region of the powder composition to be mixed. It can be advantageous, if the rotation speed and/or direction of the individual mixing shaft(s) is adjusted during the whole production process. Vertical movement of the mixing elements might be combined with a horizontal movement.

When the mixing element is introduced in the powder, the rotation speed is typically slower compared to the rotation speed which is used for mixing the intermediate region of the first and the second powder. When removing the mixing element from the powder composition, the rotation speed is typically also slower compared to the rotation speed which is used for mixing the intermediate region of the first and second powder.

According to one embodiment, the rotating mixer element(s) is/are moved into the powder composition and partially moved out of the powder composition, partially moved into the powder composition again and removed from the powder composition. By doing this, the rotation speed, the moving speed and variations of the location and positions of the individual mixers can be varied, as desired.

Speed, direction and position of the individual mixer shafts and mixing elements are typically controlled electronically (e.g. machine control). The control unit may enable the rotating speed, time, and position of the individual the mixer shaft(s) and/or mixer elements.

Generally, the mixing step is adjusted to obtain a dental milling block with a homogeneous gradient with respect to chemical composition and/or color at least in z-direction in the intermediate region of the first powder and the second powder.

It is, however, also possible to produce a dental milling block with a homogenous gradient with respect to chemical composition and/or color in z-direction and x/y-direction.

The gradient typically extends in z-direction of the dental milling block over at least 20 or at least 30 or at least 40 or at least 50% with respect to combined heights of the first and second powder.

Examples of mixing profiles which can be used are schematically shown in FIG. 4a to FIG. 4d. In the figures, the rotation speed is given on the y-axis, whereas the position of the mixing element within the powder composition is given on the x-axis.

FIG. 4a to FIG. 4d exemplify possibly relationships between rotation speed (ω) of the mixing element and its z- and x-location within the cavity of the mold for inventive embodiments. The rotation speed of the mixer can be kept constant (FIG. 4a to FIG. 4c) or can be stepped (FIG. 4d). The movement of the mixer in x-direction can be stepped (FIG. 4a to 4d). The movement of the mixer in z-direction can be linear (in and out) as shown in FIG. 5a or can follow various different schemes as shown in FIG. 4a to 4d.

Figure 5A:
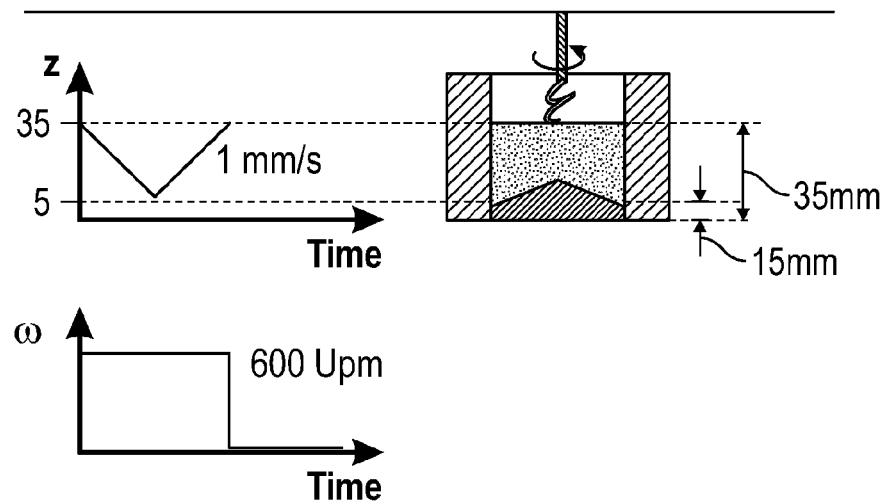
FIG. 5 (a-b) exemplifies further mixing profiles in more detail.

FIG. 5a shows a set-up for a mold in z-direction. In the cavity of the mold there is a cone of a first powder filled up to a height $H_1$ of 15 mm (dark grey). Above the first powder there is a second powder filled up to a height $H_2$ of 35 mm (light grey). A rotating mixer is introduced in the powder composition at a speed of 1 mm/s in z-direction while rotating at 600 rounds/min. After a certain time the rotating mixer is removed from the powder composition at a speed of 1 mm/s.

Figure 5B:
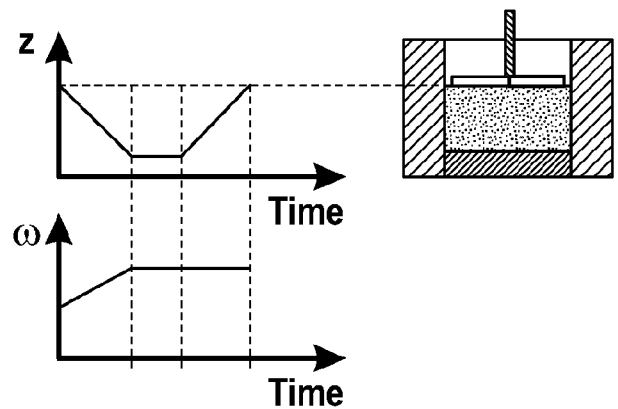

In FIG. 5b a different set-up is shown. The first and second powders are filled into the cavity of the mold layerwise and a differently shaped mixing element is used. The rotation speed of the mixing element is rather slow when entering the powder composition and increasing to a plateau once the intermediate region of the powder composition is reached. Increasing the rotation speed in the intermediate region during the process may contribute to reducing the overall mixing time. Worded differently, the at least one mixing element has a rotation speed $RS_2$ at the height $H_2$ when being introduced in the powder and a rotation speed $RS_1$ at the height $H_1$, wherein $RS_1$ differs from $RS_2$, in particular wherein $RS_1 > RS_2$.

Figure 6:
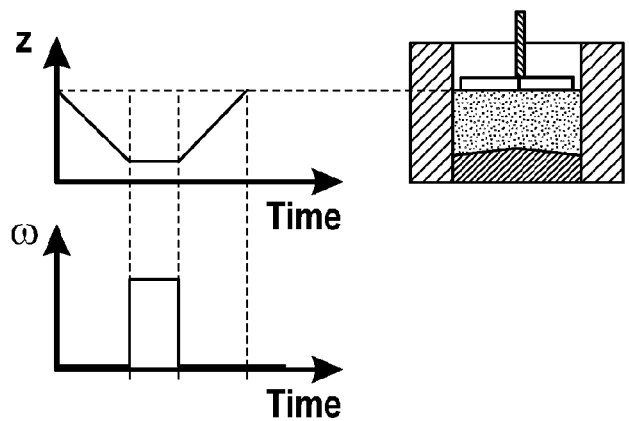
FIG. 6 exemplifies a mixing profile for a non-inventive embodiment.

In FIG. 6 a non-inventive embodiment is shown. The mixing element is rotating only during the mixing step, but not when it is introduced in and removed from the powder composition.

Figure 7A:
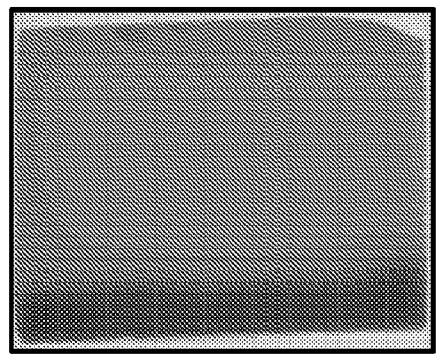
FIG. 7 (a-b) shows images of non-inventive dental milling blocks.
Figure 7B:
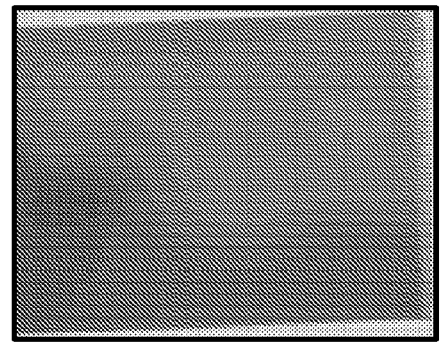

Pictures of non-inventive dental milling blocks after sintering are shown in FIG. 7a and FIG. 7b. In FIG. 7a the powders located in the cavity of the mold were not mixed at all. In FIG. 7b the powders located in the cavity of the mold were mixed, but the mixer did not rotate during introduction into and removal from the powder composition, but only during the mixing in the intermediate region of the powder composition.

Figure 7C:
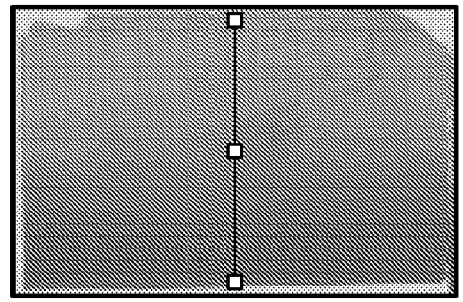
Figure 7D:
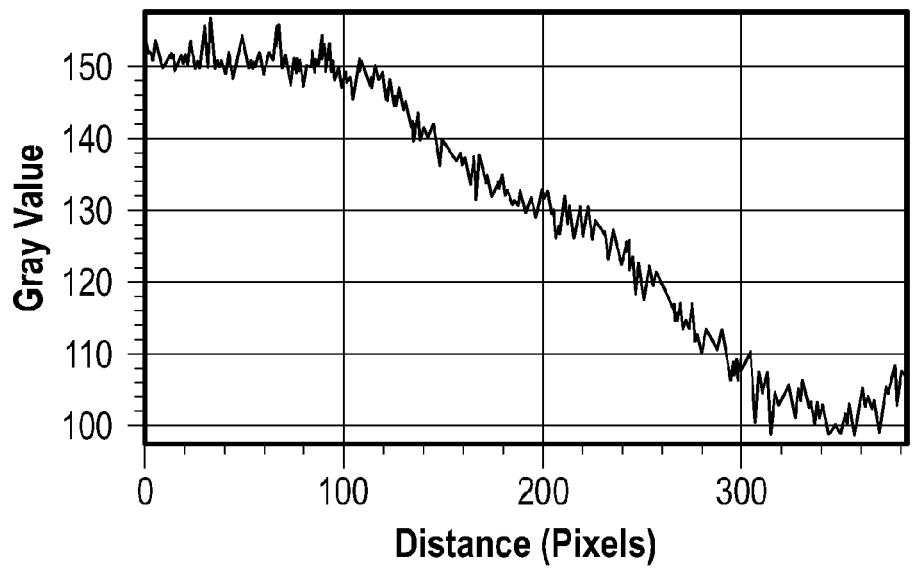

A picture of an inventive dental milling block after sintering is shown in FIG. 7c. The powders located in the cavity of the mold were mixed. The mixer rotated during introduction into the powder composition, during mixing of the powder composition in the intermediate region and during removal from the powder composition. FIG. 7d shows the profile obtained by using the plot profile function of the ImageJ software for the region of interest. A smooth color transition is shown.

In a further step, the powders located in the cavity of the mold are compacted. The compacted body is typically referred to as so-called green body.

To facilitate the compacting step(s), pressing aids can be added, if desired. Suitable pressing aids include binders, lubricating additives and mixtures thereof. The addition of pressing aids to the powder is typically done before the powder is filled in the mold.

The applied pressure is typically in the range of 5 to 400 MPa or 100 to 250 MPa.

Alternatively, the applied pressure is set so that the pressed body reaches a certain density, e.g. in the case of a compacted article of a zirconia powder a density of 2.8 g/cm$^3$ to 3.5 g/cm$^3$.

In a further step, a heat treatment or pre-sintering step can be applied to the compacted powders to obtain a porous dental milling blank, if desired.

The temperature of the heat treatment is typically in a range of 800 to 1,100° C. or 900 to 1,000° C. The heat treatment is typically applied for a duration of 10 to 150 hours or 35 to 100 hours.

The article obtained after pressing or pre-sintering the powder can be machined or sliced into any desired shape.

The powders used for producing the dental milling block can be characterized by its physical-mechanical properties.

The powders to be used in the process described in the present text should be free flowing. Free-flowing means that the particles of the powder do not stick together and flow without clumping. The flowability of a powder can also be described by its angle of repose. The lower the value, the less cohesion the individual powder particles have. Using powders with a repose angle in the range of 15 to 350 was found to be advantageous as it facilitates a laminar mixing.

In addition, the powders can be characterized by the following features alone or in combination:
a) the dominant shape of the powder particles of the powders being spherical;
b) having a BET-surface in the range of 4 to 20 m$^2$/g;
c) the powder particles being agglomerates or aggregates of smaller particles;
d) having a powder particle size d50 in the range of 25 to 150 μm;
e) having a bulk specific density of 0.9 to 2 g/cm$^3$.

A combination of features a) and b), or a) and d), or b) and c), or a), b), and c) can be advantageous.

The dominant (more than 50%) shape of the particles is typically spherical. Spherically shaped particles are typically better flowable than ground particles. Spherically shaped particles can be produced by spray drying.

Using powders with a BET surface in the above range can be beneficial as it typically allows a more homogenous sintering of the composition afterwards.

The particle size d50 of the powder should not be too high, otherwise it can become more difficult to obtain a smooth color and/or composition gradient. Using powders having similar or identical particle sizes (d50) can also be useful to facilitate the production of a smooth color and/or composition gradient during the mixing step.

More specifically, the powders to be mixed should differ from each other with respect to the following properties by not more than the given %: BET surface: not more than 20%; particle size d50: not more than 20%; Angle of repose: not more than 20%.

For producing a dental milling block different kinds of powders can be used, including ceramic powders. Examples of ceramic powder include in particular zirconia powders and alumina powders. Using ceramic powders for producing a dental milling block is sometime preferred due to its high strength.

According to one embodiment, the dental milling block to be produced is a dental zirconia milling block.

The powder composition used for producing a dental zirconia milling block comprises ceramic components and stabilizing components. Optionally, colouring components and fluorescing components can be present.

The ceramic components are typically selected from oxides of Zr, Hf, Al and mixtures thereof.

Thus, in addition to zirconia, the material of the zirconia dental milling block typically comprises oxides of Hf and optionally Al, typically in only small amounts (e.g. less than 3 wt. % for hafnia and less than 0.15 wt. % for alumina).

Stabilizing component(s) are typically selected from oxides of Y, Mg, Ca, Ce and mixtures thereof (e.g. $Y_2O_3$, MgO, CaO, $CeO_2$), wherein oxides of Y are often preferred.

If present, colouring component(s) are typically selected from oxides of Fe, Mn, Cr, Ni, Co, Er, Pr, Tb, Nd, in particular selected from the oxides of Mn, Er, Pr, Tb, Co and mixtures thereof (e.g. $MnO_2$, $Er_2O_3$, $Tb_4O_7$, CoO).

If present, a fluorescing agent is typically selected from oxides or hydroxides of Bi and mixtures thereof.

Ceramic components are typically present in an amount of 80 to 95 wt. % or 85 to 95 wt. % or 90 to 95 wt. % with respect to the weight of the dental milling block.

Stabilizing components are typically present in an amount of 3 to 12 wt. % or 5 to 10 wt. % or 6 to 10 wt. % with respect to the weight of the dental milling block.

If present, colouring components are typically present in an amount of 0.01 to 2 wt. % or 0.02 to 1.5 wt. % or 0.03 to 1.2 wt. % with respect to the weight of the dental milling block.

If present, the fluorescing agent is typically present in an amount of 0 to 1 wt. % or 0.005 to 0.8 wt. % or 0.01 to 0.1 wt. % with respect to the weight of the dental milling block.

The wt. % are calculated based on the amount of the respective oxides or the ceramic components, stabilizing components, colouring components and fluorescing agents.

For obtaining an aesthetic dental article, the following concentrations were found to be useful:
- ceramic components: 80 to 95 wt. % or 85 to 95 wt. %,
- stabilizing components: 3 to 12 wt. % or 5 to 11 wt. %,
- colouring components: 0 to 2 wt. % or 0.01 to 1.5 wt. %,
- fluorescing agent: 0 to 1 wt. % or 0.005 to 0.8 wt. %, wt. % with respect to the weight of the porous dental milling block.

According to one embodiment, the powders used for producing the dental milling block are characterized as follows:
- $ZrO_2$ content: 70 to 98 mol % or 80 to 97 mol %,
- $HfO_2$ content: 0 to 2 mol % or 0.1 to 1.8 mol %,
- $Y_2O_3$ content: 1 to 15 mol % or 1.5 to 10 mol % or 2 to 5 mol %,
- $Al_2O_3$ content: 0 to 1 mol % or 0.005 to 0.5 mol % or 0.01 to 0.1 mol %.

According to a further embodiment, the powders used for producing the dental milling block are characterized as follows:
- $ZrO_2$ content: 90 to 98 mol %,
- $HfO_2$ content: 0 to 2 mol %,
- $Y_2O_3$ content: 3 to 5 mol %,
- $Al_2O_3$ content: 0 to 0.1 mol %.

A higher $Y_2O_3$ content typically leads to an increase of the cubic crystal phase in the zirconia ceramic material after sintering the material to final density. A higher content of the cubic crystal phase may contribute to a better or higher translucency.

According to one embodiment the material of the porous dental zirconia article contains about 3, 4 or 5 mol % yttria. It has been found that these materials are particularly useful for producing an aesthetic zirconia dental restoration in a firing process as described in the present text.

In another embodiment, the powders used for producing the dental milling block comprise:
- $ZrO_2+HfO_2$: 90 to 95 wt. %;
- $Y_2O_3$: 4 to 10 wt. %;
- $Al_2O_3$: 0 to 0.15 wt. %;
- colouring oxides: 0.01 to 2 wt. %;
wt. % with respect to the weight of the respective powder.

There is no need for alumina to be present, however, the presence of a small amount of alumina may be beneficial as it may contribute to a better hydrothermal stability of the zirconia article after sintering. However, too high an amount of alumina may have a negative impact on the translucency of the zirconia article after sintering. Thus, alumina may be present in an amount of 0 to 0.15 wt. %, or 0.001 to 0.12 wt. % or 0.01 to 0.1 wt. %.

As for producing the dental milling block described in the present text at least two powders are used which differ from each other with respect to chemical composition and/or color, the respective powders may differ from each other with respect to yttria content and/or amount or nature of coloring components.

According to one embodiment, powder A has an yttria content being lower than the yttria content of powder B. After sintering, the respective compositions will have different translucency. The region with the higher yttria content is typically more translucent than the region with the lower yttria content.

According to another embodiment, powder A has a higher content of coloring components than powder B.

Suitable powders can have the following formulation and properties:

First Powder
- Ceramic components: more than 80 wt. %,
- Stabilizing components: yttria in an amount of 1 to 5 mol %, or 2 to 3 mol %,
- Coloring components: 0 to 2 wt. % (based on the respective oxide of the coloring component),
- having a BET-surface in the range of 4 to 20 m²/g,
- having a particle size d50 in the range of 25 to 150 μm,
- having a repose angle of 15 to 35°.

Second Powder
- Ceramic components: more than 80 wt. %,
- Stabilizing components: yttria in an amount of 1 to 5 mol %, or 4 to 5 mol %,
- Coloring components: 0 to 2 wt. % (based on the respective oxide of the coloring component),
- having a BET-surface in the range of 4 to 20 m²/g,
- having a particle size d50 in the range of 25 to 150 μm,
- having a repose angle of 15 to 35°.

For producing the dental milling block described in the present text, the first and the second powder, however, differ from each other at least with respect to the amounts of stabilizing components and/or coloring components being present in the respective powder.

After compacting the powder and the optional pre-sintering step, the material of a pre-sintered dental milling block can typically be characterized by the following features alone or in combination: BET surface: 5 to 20 m$^2$/g; density: 2.5 to 4 g/cm$^3$; average grain size: 50 to 200 nm. The combination of features a) and b); a) and c); a), b) and c) is sometimes preferred.

Using a dental zirconia milling block, where the material has a BET surface in the range specified above, is sometimes advantageous, because it ensures an adequate sintering activity of the material before and during a later sintering process.

Without wishing to be bound to a certain theory, it is believed that, if the BET surface is too high, there are too many pores in the porous dental zirconia article to be sintered. This might negatively influence the sintering of the article and make it more difficult to achieve a dental zirconia article having adequate strength and/or translucency. If on the other hand the BET surface is too low, it is believed that the porous zirconia article does not have an adequate sintering activity. This might negatively influence the sintering behaviour (e.g. sintering shrinkage, outgassing of remaining sintering aids) of the porous dental zirconia article during the first heat-treating step. When referring to the BET surface, in this context the surface of the calcined dental milling block is meant, not of the powder composition used for producing the block.

Alternatively, or in addition, the material of a pre-sintered dental milling block can be characterized by the following parameters alone or in combination:
- a) biaxial flexural strength: 15 to 55 MPa determined according to ISO 6872:2015 adapted to measurement in porous state (measurement set up: 3.6 mm punch diameter, 0.1 mm/min load speed, 2 mm sample thickness, support ball diameter 6 mm, 14 mm diameter of supporting balls);
- b) Vickers hardness: 15 to 150 (HV 0.5) or 20 to 140 (HV 0.5).

If desired, the respective features can be determined as described in the example section.

If the Vickers hardness of the material is too low, the machinability could negatively affect the quality (edge chipping or breaking of the workpiece) as well as in the ease of manual reworking to individualize the frame of a dental restoration or a monolithic restoration. If the Vickers hardness of the material is too high, the wear of the machining tools may increase and shorten tool life to an unacceptable level or the tool could break and destroy the workpiece.

It was found that, if the biaxial flexural strength of the material is too low, the material may tend to crack during the milling process or during the manual finishing by a dental technician. On the other hand, if the biaxial flexural strength of the material is too high, the processing of the material by a milling machine is often not possible with reasonable efforts. The milling tool used or the milled material sometimes tend to chip or break. In such a case, the shaping of the material had to be done by grinding, e.g. using a Cerec™ grinding machine (Sirona).

The dental milling block is typically provided to the customer in a form allowing the mounting of the dental milling block to a milling machine.

Either the top or bottom surface of the zirconia dental milling blank typically contains a marking element (e.g. printing or carving) which facilitates the correct orientation of the dental milling block in a milling machine.

Attaching or fixing the dental zirconia milling blank to a machining device, especially to the clamping appliance(s) of such a device, can also be accomplished by providing the blank with suitable means therefore. Suitable means include frame(s), notch(es), stub(s), mandrels and combinations thereof.

In another embodiment, the dental milling block is fixed to or contained in a holding device. The holding device containing the dental milling block may then function as a means for attaching the blank to a machining device. Fixing of the dental milling block to a holding device can be affected by clamping, gluing, screwing and combinations thereof. Useful holding devices include frames (open and closed), stubs or mandrels. Using a holding device may facilitate the production of the dental article with a machining device. Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The dental milling block has typically the shape of a blank or cuboid or disc.

If the dental milling block has the shape of a cuboid, the zirconia dental milling block has typically the following dimensions: x-dimension: 12 to 45 mm, or 15 to 40 mm, y-dimension: 12 to 70 mm, or 15 to 60 mm, z-dimension: 10 to 40 mm, or 15 to 25 mm.

If the dental milling block has the shape of a disc, the dental zirconia milling blank has typically the following dimensions: x, y-dimension: 90 to 110 mm, or 95 to 105 mm, z-dimension: 5 to 35 mm, or 10 to 30 mm.

Further embodiments, which are sometimes preferred, are described below:

Embodiment 1

A process of manufacturing a dental milling block as described in the present text, wherein the first and second powder are characterized by a repose angle of 15 to 350 and a powder particle size d50 of 25 to 150 μm.

Embodiment 2

A process of manufacturing a dental milling block as described in the present text, wherein the first and second powder are characterized by a repose angle of 15 to 350 and a powder particle size d50 of 25 to 150 μm and wherein the powders to be mixed differ from each other with respect to the following properties by not more than the given %: particle size d50: not more than 20%; angle of repose: not more than 20%.

Embodiment 3

A process of manufacturing a dental milling block as described in the present text, wherein the mixing element is moved in z-direction over a distance of less than 80% of height H$_2$ and wherein the at least one mixing element has a helical or auger shape.

Embodiment 4

A process of manufacturing a dental milling block as described in the present text, wherein the at least one mixing element is moved or moveable in x/y-direction and the powder to be mixed in the intermediate region extends to less than 90% of the dimension of the cavity in x/y-direction of the cavity.

Embodiment 5

A process of manufacturing a dental milling block as described in the present text, wherein the first powder is applied in form of a cone and wherein the first and second powder have a repose angle of 15 to 35°.

Embodiment 6

A process of manufacturing a dental milling block as described in the present text, wherein the first and second powder are characterized by a repose angle of 15 to 35° and a powder particle size d50 of 25 to 150 μm and wherein the at least one mixing element is moved or moveable in x/y-direction and the powder to be mixed in the intermediate region extends to less than 90% of the dimension of the cavity in x/y-direction of the cavity.

Embodiment 7

A process of manufacturing a dental milling block as described in the present text, wherein the first and second powder are characterized by a repose angle of 15 to 35° and the at least one mixing element has a rotation speed $RS_2$ at the height $H_2$ and a rotation speed $RS_1$ at the height $H_1$, wherein $RS_1$ is different from $RS_2$.

Embodiment 8

A process of manufacturing a dental milling block as described in the present text, wherein the first and second powder are characterized by a repose angle of 15 to 35° and the at least one mixing element has a rotation speed $RS_2$ at the height $H_2$ and a rotation speed $RS_1$ at the height $H_1$, wherein $RS_1 > RS_2$.

Contrary to process described in the prior art, according to the invention, only a certain portion of the powder composition is mixed, but not the complete overall volume.

Further, the process described in the present text does typically not contain the following steps alone or in combination: a) providing the surface of the first and/or second powders with a pattern; b) applying a third powder on top of the second powder, wherein the third powder is different in its chemical composition from the first and second powder.

The invention is also related to a process of producing a dental restoration.

This process comprises the steps of
  manufacturing a dental milling block according to a process described in the present text,
  applying heat to the compacted powder to obtain a heat-treated dental milling block,
  machining a dental restoration from the heat-treated dental milling block,
  sintering the dental restoration.

The machining can be done using commercially available milling devices, such as Cercon™ from DentsplySirona. As desired, the sintering can be done by applying either of the following heat treatment steps: a) sintering temperature 1,350 to 1,600° C., heating rate 1 to 7° C./sec; b) sintering temperature 1,350 to 1,600° C., heating rate 1 to 30° C./min.

The dental restoration may have different shapes, including the shape of a dental crown, bridge, veneer, inlay or onlay.

The invention also relates to a kit of parts comprising the mold as described in the present text, the mixing unit as described in the present text, a first powder and a second powder as described in the present text.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar based on sea level).

Methods

Elemental Composition

If desired, the elemental composition can be determined by X-ray fluorescence spectrometry (XRF), e.g. with the ZSX Primus II from Rigaku, Japan. This method is especially suited for the analysis of solids, e.g. zirconia ceramics or glass materials.

Fluorescence

If desired, the samples are placed in an UV-light box used for inspection of e.g. thin layer chromatography plates. Fluorescence can be detected by the human eye by the lightening up of the sample against the black background.

BET Surface

If desired, the BET surface of a porous article can be determined as follows: Total pore volume and average pore diameter can be analyzed with the use of $N_2$ sorption isotherms and BET surface area analysis. Samples of around 0.1-2 grams can be cut (if necessary) from larger samples in order to be inserted into the sample tubes. All samples are degassed in vacuum for more than 1 h at 120° C. before analysis. The samples are then analyzed by adsorption and desorption of $N_2$ gas with a Belsorb II (distributed by Robotherm Präzisionsmesstechnik, Bochum, Germany) in a 9 mm cell with 2 cm bulb and with a 5 mm glass rod. At temperature of liquid nitrogen, absorption data points are collected from 0.1 to 0.99 p/p0 and desorption points collected from 0.99 to 0.5 p/p0. The specific surface area S is calculated by the BET method at p/p0 0.25-0.3 (details regarding calculation see Belsorb Analysis Software User Manual Operating Manual, Chapter 12, Bel Japan. INC).

Density

If desired, the density of the sintered material can be measured by an Archimedes technique. The measurement is made on a precision balance (identified as "BP221S" from Sartorius AG, Göttingen, Germany) using a density determination kit (identified as "YDK01" from Sartorius AG). In this procedure, the sample is first weighed in air (A), then immersed in a solution (B). The solution is a 0.05 wt. % tenside solution (e.g. "Berol 266", Fa. Hoesch) in DI water. The density is calculated using the formula $\rho=(A/(A-B))\rho 0$, where $\rho 0$ is the density of water.

In the case that the material possesses a regular shape (e.g. of a cuboid), the density can simply be determined by measuring the dimensions x, y, and z (e.g. with a sliding caliper (identified as "IP67" from Mitutoyo, Japan)) and the weight m of the sample (e.g. with a precision balance (identified as "BP221S" from Sartorius AG, Göttingen, Germany)). The density is calculated using the formula $\rho=m/(x*y*z)$.

Bulk Density of Powder

The bulk density can either be taken from the material data sheets provided by the supplier of the powder or can be determined according to DIN EN ISO 23145-2, where the untapped density of granulated or ungranulated powder is determined by a constant-volume measuring method.

Porosity

If desired, the porosity can be determined as follows: Porosity=(1−(density of porous material/density of sintered material))×100. As described above ("Density" section), the density of the porous material can be calculated by the division of weight and volume. Volume can be obtained by geometrical measurements.

Pore Volume:

The pore volume of a porous zirconia body $V_P$ can be determined by subtracting the volume of the zirconia material in the porous body ($V_Z$=weight of the porous body/density of the zirconia material) from the entire volume of the porous body (e.g. $V_B=x*y*z$): $V_P=V_B-V_Z$. For the present text, the density of the sintered zirconia material is defined as 6.08 g/cm$^3$. This value is considered sufficiently precise for determining the pore volume of a porous zirconia body.

Particle Size (Suitable for Micro-Sized Particles)

If desired, the particle size distribution including the particle size (d50) per volume can be determined by laser diffraction with a Mastersizer 2000 (Malvern) particle size detection device applying the Fraunhofer approximation. During the measurement, ultrasonic is typically used to accurately disperse the sample. For water-insoluble particles, water is typically used as dispersant.

Average Grain Size (Pre-Sintered or Sintered Body)

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Biaxial Flexural Strength

If desired, the biaxial flexural strength of pre-sintered material can be determined according to ISO 6872:2015 with the following modifications: The pre-sintered sample is sawn into wafers with a thickness of 2+/−0.1 mm using a dry cut saw. The diameter of the samples should be 17+/−2 mm. The parallel large faces of the wafer are ground using silicon carbide sandpaper (P2500). Each wafer is centred on a support of three steel balls (diameter of the balls 6 mm) with a support diameter of 14 mm. The punch diameter in contact with the wafer is 3.6 mm. The punch is pushed onto the wafer at a rate of 0.1 mm per min. A minimum of 15 samples is measured to determine the average strength. The tests can be conducted using an Instron 5566 universal testing machine (Instron Deutschland GmbH).

Vickers Hardness

If desired, the Vickers hardness can be determined according to ISO 14705 with the following modifications: The surface of the pre-sintered samples is ground using silicon carbide sandpaper (P2500). The surface of the sintered samples is polished with 20 μm diamond suspension. The test forces are adjusted to the hardness level of samples. Used test forces can be between 0.2 kg and 2 kg and are applied for 15 s each indentation. A minimum of 10 indentations is measured to determine the average Vickers hardness. The tests can be conducted with a hardness tester Leco M-400-G (Leco Instrumente GmbH).

Scanning Electron Microscope (SEM) Images

If desired images of the various states of the powders and powder compositions (e.g. before and after sintering) can be produced by SEM.

Color Gradient

If desired, images of a color gradient in a colored powder mixtures can be further analysed using the plot profile function of ImageJ software (Java-based image processing program developed at the National Institute of Health and the Laboratory for Optical and Computational Instrumentation; not subject to copyright protection). A color gradient is typically considered homogenous, if the image plot shows an essentially smooth transition from the light grey area to the dark grey area in the region of interest.

In more detail: A digital picture is taken from the area of interest. The area of interest is preferably a plate prepared from the body, perpendicular to the intermediate region of powders A and B. The picture might be taken using transition light through the plate, e.g. by putting the plate on a light table. The pixels of the picture are a local measure of the optical properties of the material and can be analysed using a picture analysis software. A file/picture is opened and a line is selected in the picture using the "straight" button. This line can be analysed by using the "plot profile" function in the "analysis" section. The profile of the grey values is plotted and the gradient can be observed as a flat or more jagged curve. For a more detailed analysis, the data of the profile data can be transferred numerically and further analysed, if desired.

L*a*b* Values/Translucency

If desired, the translucency and L*a*b* values of the articles described in the present text can be evaluated with the following procedure: A test piece in the shape of a disc with an approximate thickness of 1±0.05 mm and an area of measurement of at least 10 mm in diameter is provided. For preparation of the test pieces the pre-sintered sample is sawn into wafers with a thickness of approximately 1.3 mm using a dry cut saw. The parallel large faces of the wafer are ground using silicon carbide sandpaper (P2500). The ground samples are sintered in an appropriate furnace to a sintered sample with a thickness of 1±0.05 mm. The sintered sample is measured as fired with a spectrophotometer (X-Rite Color i7, Grand Rapids, USA) in reflectance mode against a white and a black background to obtain the opacity (contrast ratio)

of the material. The translucency T is calculated according to T=100%−opacity (in percent). Higher values of translucency are indicative of greater transmission of light, and less opacity.

Flowability/Angle of Repose

The flowability of powders can be determined by a repose angle measurement according to the standard DIN ISO 4324—"Pulver und Granulate, Bestimmung des Schüttwinkels".

On this measurement a funnel with defined outlet diameter (Ø=10 mm) is filled with a prescribed amount of powder. After opening the outlet the powder trickles on an acrylic glass plate with a prescribed diameter (Ø=100 mm). After the amount of powder is fully run through, the height of the standing cone is measured. The calculation of the repose angle occurs to following formula:

tan □=2×$H$/100 with □=repose angle; $H$=Height of the cone

The smaller the angle the more fluid the powder is. For a classification of the powders following rating can be used:

| Flowable properties | Repose Angle in ° |
|---|---|
| Excellent | <30 |
| Good | 31-35 |
| Satisfying (No flow additives necessary) | 36-40 |
| Moderate (Powder flow can stop) | 41-45 |
| Bad (Must be encouraged to flow) | 46-55 |
| Very Bad | 56-65 |
| Insufficient | >66 |

Materials

| | |
|---|---|
| Zirconia powder A (ZP-A) | white zirconia powder (4Y-ZP) |
| Zirconia powder B (ZP-B) | $Fe_2O_3$ doped zirconia powder (4Y-ZP) |
| Zirconia powder C (ZP-C) | white zirconia powder (3Y-ZP) |
| Zirconia powder D (ZP-D) | white zirconia powder (5.5Y-ZP) |
| Zirconia powder E (ZP-E) | $Cr_2O_3/Fe_2O_3$ doped zirconia powder 4Y-ZP |

Powder A

As Powder A (ZP-A) a commercially available white (uncolored) zirconia powder was used. ZP-A had the following properties: BET surface: 8 m²/g, particle size d50: 53 μm, bulk density of powder: 1.55 g/cm³, repose angle: 24°.

Powder B

As Powder B (ZP-B) a commercially available zirconia powder which has been doped with an Fe-component, e.g. by applying an aqueous solution containing a soluble iron salt, drying and milling the respective powder composition was used. ZP-B had the following properties: BET surface: 8 m²/g, particle size d50: 52 μm, bulk density of powder: 1.64 g/cm³, repose angle: 23°.

Powder C

As Powder C (ZP-C) a commercially available white (uncolored) zirconia powder was used. ZP-C had the following properties: BET surface: 8 m²/g, particle size d50: 53 μm, bulk density of powder: 1.49 g/cm³, repose angle: 25°.

Powder D

As Powder D (ZP-D) a commercially available white (not colored) zirconia powder was used. ZP-D had the following properties: BET surface: 8 m²/g, particle size d50: 53 μm, bulk density: 1.50 g/cm³, repose angle: 23°.

Powder E

As Powder E (ZP-E) a commercially available zirconia powder was used which has been doped with an Cr/Fe-component, e.g. by applying an aqueous solution containing a soluble Cr/iron salt, drying and milling the respective powder composition. ZP-E had the following properties: BET surface: 8 m²/g, particle size d50: 52 μm, bulk density of powder: 1.55 g/cm³, repose angle: 23°.

Figure 8:
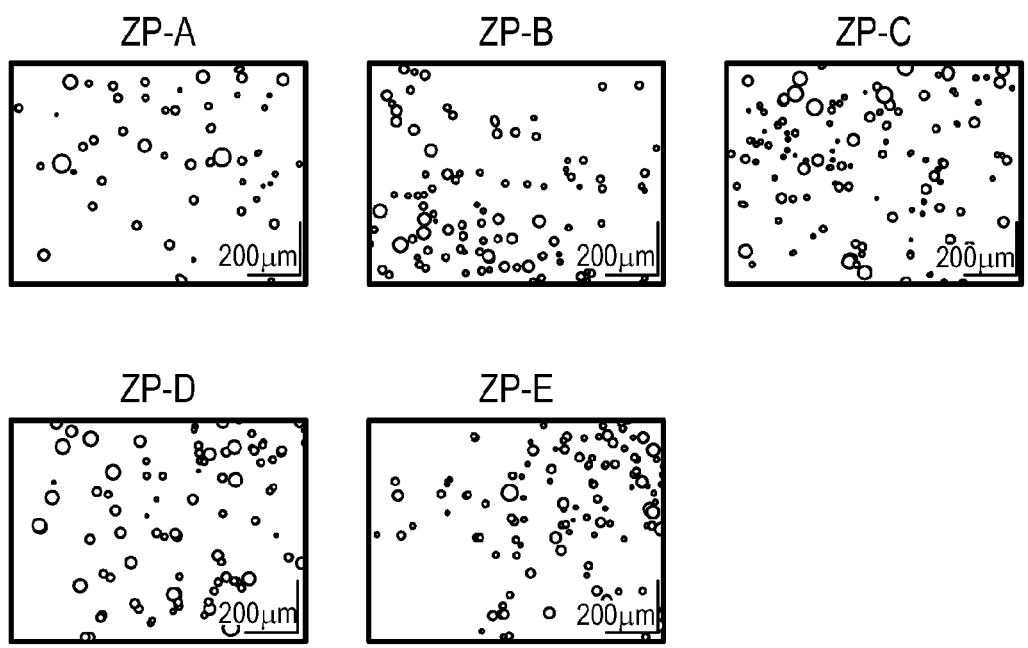
FIG. 8 shows microscope pictures (binary format) of different zirconia powders.

FIG. 8 shows microscope pictures of the zirconia powders ZP-A, ZP-B, ZP-C, ZP-D and ZP-E, transformed to binary format, indicating the dominant spherical character of the powder particles. The pictures were taken randomly.

Inventive Example 1

A mold with a cavity was provided having the dimensions: z-direction: 35 mm; diameter: 25 mm.

A cone of ZP-A was filed in the mold up to a maximum height of $H_{PA}$=15 mm. On top of ZP-A, ZP-B was filled up to a height $H_{PB}+H_{PA}$=35 mm.

A mixing unit comprising a motor and a mixing shaft with a mixing element made of plastic was provided. The mixing element was helical shaped (height: 6 mm; diameter: 6.5 mm; incline: 6 mm). The mixing shaft and mixing element essentially correspond to the shape of the mixer shown in FIG. 1c.

The mixer unit was placed on the top powder surface and started. The rotation speed was 600 rounds/min, equal to 10 rounds/s. The rotating mixing element was introduced 30 mm at a speed of 1 mm/s in z direction down to in the region the volume of ZP-A and withdrawn mediately at the same speed of 1 mm/s. The position in x and y were kept constant. The rotating mixing shaft with the mixing element was removed from the powder composition. The experimental set-up is shown in FIG. 5a.

Figure 9A:
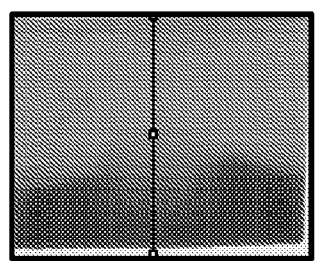
FIG. 9 (a-b) shows an image of the sintered body of example 1 and the related plot profile.

The obtained powder mixture was compacted using a pressure of about 12 MPa for about 2 min. The compact was thermal treated at 900° C. for 2 h and then cut through the centre to obtain a plate. This plate was thermal treated at a temperature of about 1,550° C. for 4 minutes. An image of the cut plate is shown in FIG. 9a.

Figure 9B:
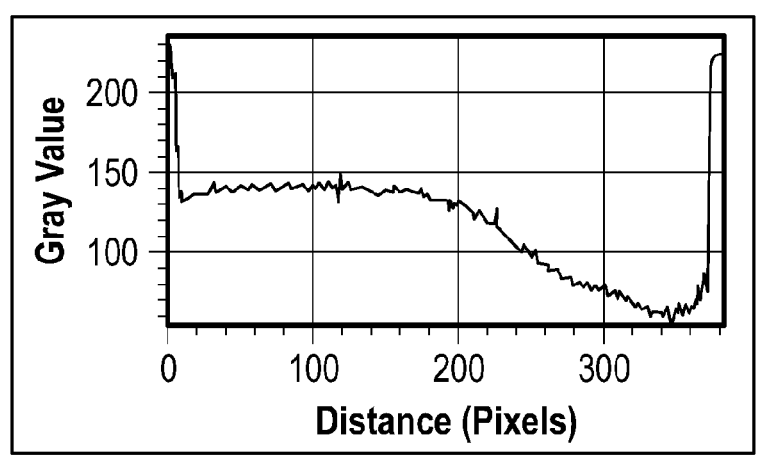

Observation:

The mixing zone in x,y-direction was limited to about ⅓ of the dimension of the block in x and y, proving that by using the process described in the present text a defined mixing of small powder regions within a rather small overall powder volume thereby obtaining a smooth gradient in the region of interest is possible. A profile plot of grey values of the picture in z direction through the mixed zone indicates a smooth colour gradient. A profile plot of grey values of the picture in z direction through the unmixed zone indicates a sharp colour gradient (FIG. 9b).

Inventive Example 2

A mold with a cavity was provided having the dimensions: z-direction: 35 mm; diameter: 25 mm.

A cone of ZP-A was filed in the mold up to a maximum height of $H_{PA}$ (1.25;1.25)=15 mm. On top of the layer of ZP-A, a layer of ZP-B was filled up to a height $H_{PB}+H_{PA}$=35 mm.

A mixing unit comprising a motor and a mixing shaft with a mixing element made of plastic was provided. The mixing element was helical shaped (height: 6 mm; diameter: 6.5 mm; incline: 6 mm). The mixing shaft and mixing element essentially correspond to the shape of the mixer shown in FIG. 1c.

Figure 10A:
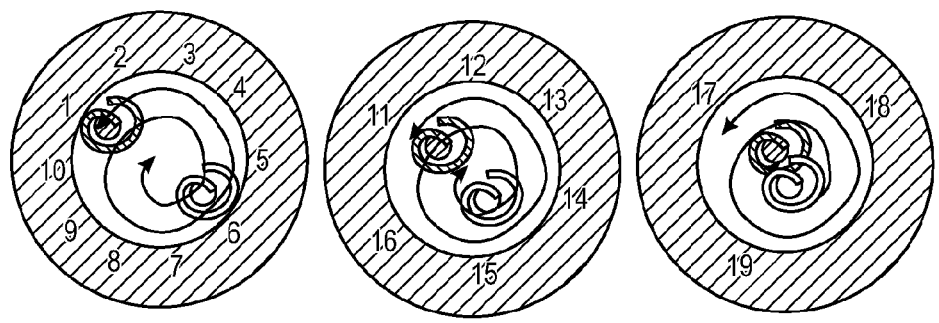
FIG. 10 (a-c) shows the experimental set-up of example 2, an image of the sintered body of example 2 and the related plot profile.
Figure 10A:
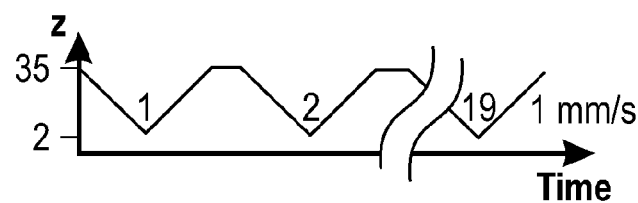
Figure 10A:
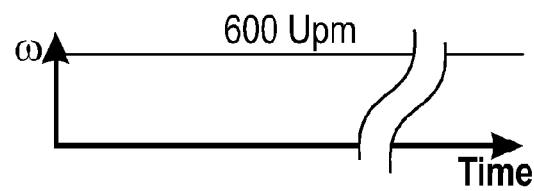

The mixer unit was placed on the top powder surface and started. The rotation speed was 600 rounds/min, equal to 10 rounds/s. At the starting position at the edge of the mold (position 1) the rotating mixing element was introduced in the powder for a distance of 33 mm at a speed of 1 mm/s in z direction down to in the region of ZP-A and withdrawn mediately at the same speed of 1 mm/s. The position of the mixer was changed (position 2) in x/y-direction for an overall distance of 6 mm, but the mixer was kept at the edge of the mold. Another mixing in z-direction with the same parameters as used in position1 was done. This was repeated 10 times in order to mix the circumference of the mold (positions 1 to 10). Then, a smaller circumference path was adjusted and another 6 mixing cycles in z were done (positions 11 to 16). Finally, another 3 mixing cycles almost in the centre were done (positions 17 to 19). The experimental set-up is shown in FIG. 10a. After this helix-like mixing of the powder composition, the rotating mixing shaft with the mixing element was removed.

Figure 10B:
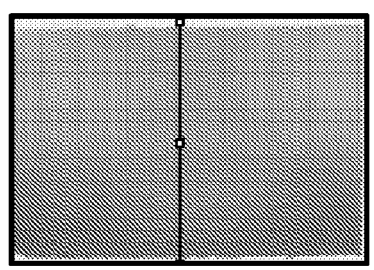

The obtained powder mixture was compacted using a pressure of about 82 MPa for about 2 min. The compact was thermal treated at 900° C. for 2 hours. and then cut through the centre to obtain a plate. This plate was thermal treated at a temperature of about 1,550° C. for 4 minutes. An image of the cut plate is shown in FIG. 10b.

Figure 10C:
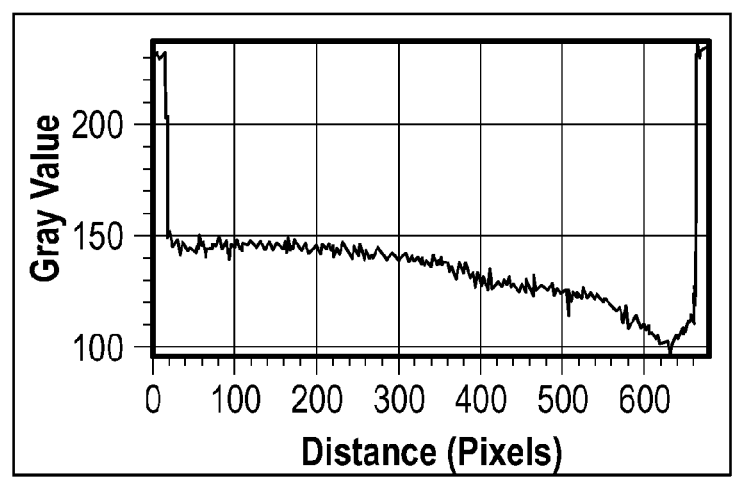

Observation:

The unmixed lower region of ZP-B was smoothly transitioned to an unmixed upper region of ZP-A by an intermediate region of mixed powders ZP-B and ZP-A. No individual layers were visible. A profile plot of grey values of the picture in z direction through the mixed zone indicates a smooth colour gradient. In FIG. 10c the photograph of FIG. 10b has been analysed with the software ImageJ for grey values. As can be taken from the plot, in the region of interest there is a smooth transition from the light grey area to the darker grey area.

Inventive Example 3

A mold with a cavity was provided having the dimensions: z-direction: 35 mm; diameter: 25 mm.

A layer of ZP-C was filed in the mold up to a height of $H_{PC}$=13 mm. On top of the layer of ZP-C, a layer of ZP-D was filled up to a height $H_{PC}$+$H_{PD}$=13 mm+15 mm=28 mm.

A mixing unit comprising a motor and a mixing shaft with a mixing element made of plastic was provided. The mixing element was helical shaped (height: 6 mm; diameter: 6.5 mm; incline: 6 mm). The mixing shaft and mixing element essentially correspond to the shape of the mixer shown in FIG. 1c.

The mixer unit was placed on the top powder surface and started. The rotation speed was 200 rounds/min, equal to 3.33 rounds/s. The rotating mixing element was introduced 23 mm at a speed of 1 mm/s in z direction down to in the region of ZP-D and moved vertically by hand, following a helix like path from the edge of the mold to the centre and back. After that, the z position was moved to about 18 mm and again, moved vertically by hand, following a helix like path from the edge of the mold to the centre and back. After that, the z position was moved to about 13 mm and again, moved vertically by hand, following a helix like path from the edge of the mold to the centre and back. After that, the z position was moved to about 8 mm and again, moved vertically by hand, following a helix like path from the edge of the mold to the centre and back. After that, the z position was moved to about 3 mm and again, moved vertically by hand, following a helix like path from the edge of the mold to the centre and back. The rotating mixing shaft with the mixing element was removed from the powder composition.

After the mixing step, the obtained powder mixture was compacted using a pressure of about 200 MPa for about 3 min. The compact was thermal treated at about 920° C. for 2 hours and then cut through the centre to obtain a plate. This plate was thermal treated at a temperature of about 1,500° C. for 2 h.

Figure 11:
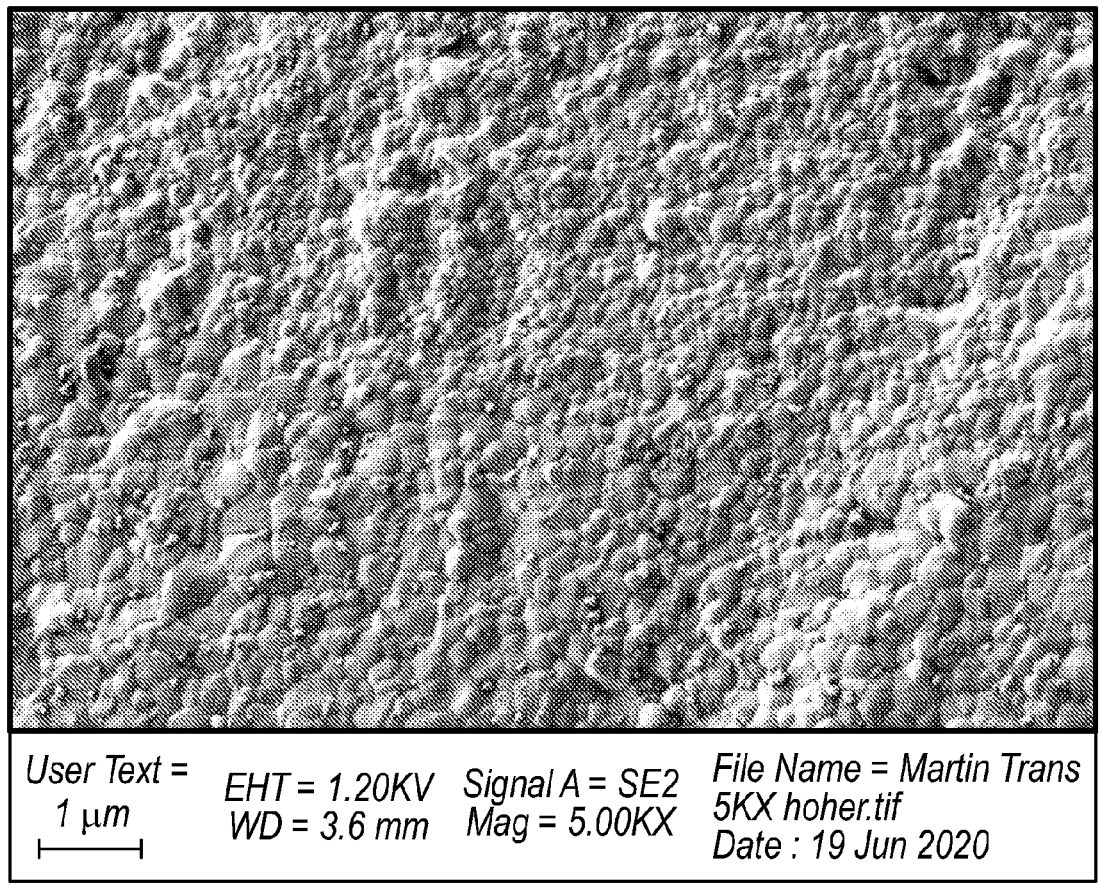
FIG. 11 shows an SEM image of the sintered body obtained in example 3.

Observation:

Similar to Inventive Example 2, a smooth transition between the respective regions remained also after sintering. The microstructure of the obtained sintered zirconia body was further analysed with SEM (FIG. 11). Larger grains are related to 5.5 mol % yttria containing zirconia material (ZP-D), smaller grains are related to 3 mol % yttria containing material (ZP-C). As shown in the SEM picture, the mixing of the respective powders took place on a microstructure level as larger grains can be found in small grained areas and small grains can be found in large grained areas.

Inventive Example 4

A mold with a cavity was provided having the dimensions: z-direction: 35 mm; diameter: 25 mm.

A layer of ZP-A was filed in the mold up to a height of $H_{PA}$=6 mm. On top of the layer of ZP-A, a layer of ZP-B was filled $H_{PB}$=28 mm up to a height $H_{PB}$+$H_{PA}$=34 mm.

Figure 12A:
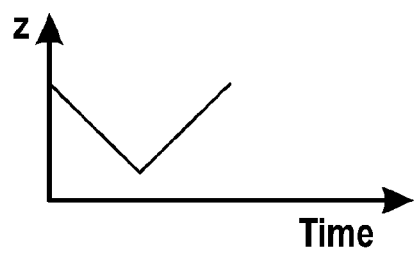
FIG. 12 (a-d) shows the experimental set-up of example 4 an image of the sintered body of comparative example 1 and the related plot profile.
Figure 12B:
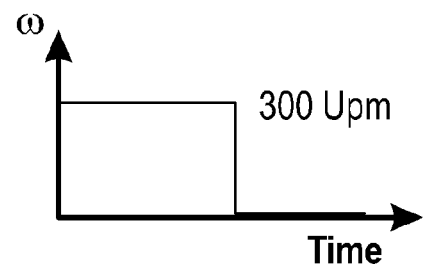

A mixing unit comprising a motor and a mixing shaft with mixing elements made of plastic was provided. The mixing element was blade shaped (height: 6 mm; diameter: 6.5 mm; incline: 6 mm). The mixing shaft and mixing element essentially correspond to the shape of the mixer shown in FIG. 1b. The mixer unit was placed on the top powder surface and started. The rotation speed was 300 rounds/min, equal to 5 rounds/s. The rotating mixing element was introduced by hand in z direction slowly down to in the region the volume of ZP-B and withdrawn. The rotating mixing shaft with the mixing element was removed from the powder composition. The mixing profile is shown in FIG. 12a/12b.

Figure 12C:
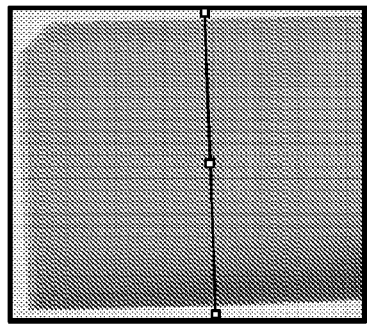

The obtained powder mixture was compacted using a pressure of about 82 MPa for about 2 min. The compact was thermal treated at 920° C. for 2 hours and then cut through the centre to obtain a plate. This plate was thermal treated at a temperature of about 1,500° C. for 2 h. An image of the cut plate is shown in FIG. 12c.

Figure 12D:
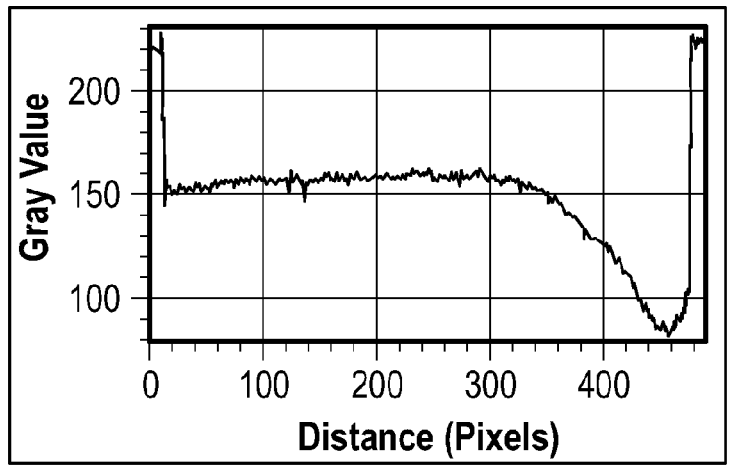

Observation:

Similar to Inventive Example 2, the smooth transition between the respective regions remained also after sintering. In FIG. 12d the photograph of FIG. 12cb has been analysed with the software ImageJ for grey values. As can be taken from the plot, in the region of interest, there is a smooth transition from the light grey area to the darker grey area.

Comparative Example 1

Inventive Example 4 was repeated, but the mixing shaft was not rotating when introduced and removed from the powder composition.

Figure 13A:
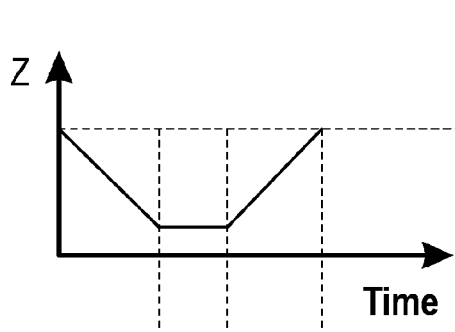
FIG. 13 (a-d) shows the experimental set-up of comparative example 1 and an image of the sintered body.
Figure 13B:
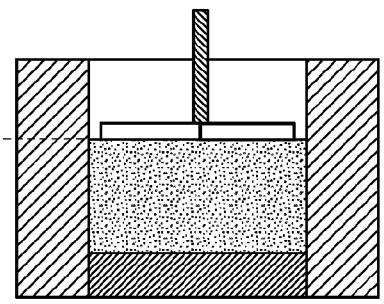
Figure 13C:
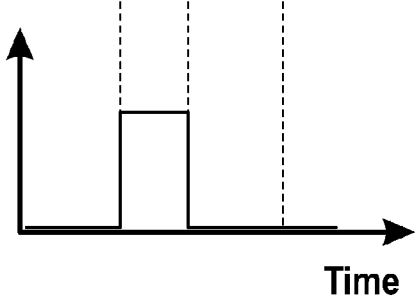
Figure 13D:
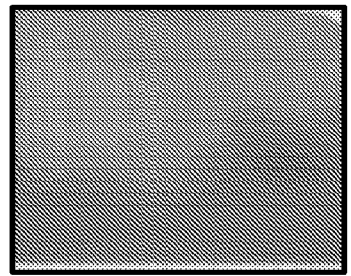

The experimental set-up is shown in FIG. 13a to FIG. 13c. An image of the cut plate after the compacting and sintering step is shown in FIG. 13d.

Observation:

Compared to Inventive Example 4, the sintered sample of Comparative Example 1 showed a less uniform and inhomogenous color gradient.

The invention claimed is:

1. A process of manufacturing a dental milling block, the process comprising the steps of
providing a mold with a cavity having a z-direction and an x/y-direction, filling the cavity partially with a first powder up to a height $H_1$, the first powder having a volume $V_{P1}$ with a top and bottom surface, introducing a second powder on top of the first powder up to a height $H_2$, the second powder having a volume $V_{P2}$ with a top and bottom surface and, the top surface of the first powder being in contact with the bottom surface of the second powder and forming an intermediate region, providing a mixer unit with at least one rotatable mixing element, introducing the mixing element in z-direction into the intermediate region while it is rotating, mixing the powder located in the intermediate region by rotating the mixing element, removing the mixing element from the powder while it is rotating, and compacting the powder, optionally applying heat to the compacted powder, the first powder differing from the second powder by its physical properties and/or chemical composition and/or color.

2. The process according to claim 1, wherein the first powder and the second powder being characterized by a repose angle of 15 to 35°.

3. The process according to claim 1, wherein the first powder being applied in form of a layer or a cone.

4. The process according to claim 1, wherein the first powder and/or second powder being characterized by the following features alone or in combination:
   a) the dominant shape of the powder particles of the powders being spherical,
   b) having a BET surface of 4 to 20 m²/g;
   c) the powder particles of the first and second powder being agglomerates or aggregates of smaller particles;
   d) having a powder particle size d50 of 25 to 150 μm;
   e) having a bulk specific density of 0.9 to 2 g/cm³.

5. The process according to claim 1, wherein the powder to be mixed in the intermediate region extending to less than 95% or less than 80% of the dimension of the cavity of the mold in x/y-direction.

6. The process according to claim 1, wherein the at least one mixing element is moved in z-direction during the mixing step over a distance of less than 90% or less than 60% of height $H_2$.

7. The process according to claim 1, wherein the mixing step being adjusted to obtain a gradient with respect to its physical properties and/or chemical composition and/or color of the powders in z-direction and x/y-direction.

8. The process according to claim 7, wherein the gradient extending in z-direction at least over 20% or at least over 40% of height $H_2$.

9. The process according to claim 1, wherein the volume of the powders $V_{P1}$ and $V_{P2}$ differing from each other by not more than 60%.

10. The process according to claim 1, wherein the at least one mixing element has a rotation speed $RS_2$ at the height $H_2$ and a rotation speed $RS_1$ at the height Hi, wherein $RS_1$ is different from $RS_2$.

11. The process according to claim 1, wherein the mixer unit comprising at least 2 individually rotatable or individually shaped mixing elements.

12. The process according to claim 1, wherein the direction of the rotation and/or the rotation speed of the mixing element(s) being individually adjustable.

13. The process according to claim 1 and not comprising the step of filling into the cavity of the mold a further powder being different from the first and second powder.

14. A process of producing a dental restoration, the process comprising the steps of
   manufacturing a dental milling block according to claim 1 applying heat to the compacted powder to obtain a heat-treated dental milling block,
   machining a dental restoration from the heat-treated dental milling block, and
   sintering the dental restoration.

15. A kit of parts for manufacturing a dental milling block comprising a mold as claimed in claim 1, a mixer unit as claimed in claim 1, and a first and a second powder as claimed in claim 1.

* * * * *